United States Patent
Kim et al.

(10) Patent No.: US 10,555,932 B2
(45) Date of Patent: Feb. 11, 2020

(54) METHOD OF RESTORING ANALGESIC EFFICACY OF ALPHA2-ADRENOCEPTOR AGONISTS IN NEUROPATHIC PAIN TREATMENT

(71) Applicant: KOREA INSTITUTE OF SCIENCE AND TECHNOLOGY, Seoul (KR)

(72) Inventors: Key-Sun Kim, Seoul (KR); Seo-Yeon Yoon, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

(21) Appl. No.: 16/138,360

(22) Filed: Sep. 21, 2018

(65) Prior Publication Data

US 2019/0022067 A1    Jan. 24, 2019

Related U.S. Application Data

(62) Division of application No. 15/784,356, filed on Oct. 16, 2017, now abandoned.

(30) Foreign Application Priority Data

Oct. 17, 2016  (KR) .................. 10-2016-0134553

(51) Int. Cl.
```
A61K 31/4168    (2006.01)
A61K 31/4174    (2006.01)
A61K 31/433     (2006.01)
A61K 45/06      (2006.01)
```
(52) U.S. Cl.
CPC ...... *A61K 31/4168* (2013.01); *A61K 31/4174* (2013.01); *A61K 31/433* (2013.01); *A61K 45/06* (2013.01)

(58) Field of Classification Search
CPC ............ A61K 31/4168; A61K 31/4174; A61K 31/433; A61K 45/06
USPC ....................................................... 514/361
See application file for complete search history.

(56) References Cited

PUBLICATIONS

Kumar et al. Saudi J. Anaesth, Jan.-Mar. 2014, 8(1), p. 92-96. (Disclosed in IDS).*
Gleeson et al. Psychopharmacology (1982), 78, p. 141-146. (Disclosed in IDS).*
Yoon et al. Pain and Analgesic Mechanisms, Mar. 2015, 120(3), p. 671-677. (Disclosed in IDS).*
Sierralta et al., British Journal of Pharmacology, (1996), v.119, p. 551-554.*
Gleeson et al., "Chlorpromazine Hyperalgesia Antagonizes Clonidine Analgesia, but Enhances Morphine Analgesia in Rats Tested in a Hot-Water Tail-Flick Paradigm", Psychopharmacology, vol. 78, 1982, pp. 141-146.
Kumar et al., Saudi J. Anaesth, Jan.-Mar. 2014, 8(1), p. 92-96.
Office Action dated Sep. 28, 2017 for the corresponding Korean application No. 10-2016-0134553.
Yoon et al., Pain and Analgesic Mechanism, Mar. 2015, 120(3), p. 671-677.

* cited by examiner

*Primary Examiner* — Yong L Chu
(74) *Attorney, Agent, or Firm* — Birch, Stewart, Kolasch & Birch, LLP

(57) ABSTRACT

Provided are a pharmaceutical composition including: an alpha 2 (α2)-adrenoceptor agonist; a regulator of G-protein signaling (RGS) inhibitor, an endocytosis inhibitor, or a combination thereof; and a pharmaceutically acceptable salt, and a method of relieving pain of a subject, the method including administering the pharmaceutical composition to a subject.

13 Claims, 9 Drawing Sheets

METHOD OF RESTORING ANALGESIC EFFICACY OF ALPHA2-ADRENOCEPTOR AGONISTS IN NEUROPATHIC PAIN TREATMENT

CROSS-REFERENCE TO RELATED APPLICATIONS

This application is a Divisional of co-pending U.S. application Ser. No. 15/784,356 filed on Oct. 16, 2017, which claims the benefit of priority to Korean Patent Application No. 10-2016-0134553, filed on Oct. 17, 2016, in the Korean Intellectual Property Office, the disclosure of which is incorporated herein in its entirety by reference.

BACKGROUND

1. Field

The present invention relates to a composition including: an alpha 2 (α2)-adrenoceptor agonist; a regulator of G-protein signaling (RGS) inhibitor, an endocytosis inhibitor, or a combination thereof; and a pharmaceutically acceptable carrier, and a method of relieving pain by restoring reduced analgesic efficacy of an α2-adrenoceptor agonist in neuropathic pain by administering the composition to a subject.

2. Description of the Related Art

Alpha 2 adrenoceptor (α2AR) is coupled to G-protein and activated by epinephrine, norepinephrine, or isoprenaline. Activation of α2AR reduces a concentration of cAMP by inhibiting adenylate cyclase via $G\alpha_i$. The α2AR has three subtypes of $\alpha 2_A$, $\alpha 2_B$, and $\alpha 2_C$. Among them, the $\alpha 2_A$AR is known to be involved in regulation of blood pressure, pain perception, volatile anesthetic sparing, analgesia, and working memory enhancement (Lu, et al., 2010), and has been a therapeutic target for the related diseases. Currently, several α2AR agonists and antagonists are available in the market, but they have been used for rather limited symptoms. Among α2AR agonists, clonidine is currently used as a therapeutic agent for high blood pressure and ADHD, and dexmedetomidine is used as a sedative medication. If α2AR is used as an analgesic drug, a high dose of the drug is required to be administered. However, due to problems of severe hypotension induced by such a high dose of the drug, α2AR is not used as an analgesic drug.

The inventors of the present inventive concept previously reported that spinal RGS4, which is a protein regulating a G-protein signaling system, inhibited an opioid receptor (OR)-mediated antinociceptive effect in a formalin pain test (Yoon et al., 2015). Activated G-protein coupled receptor (GPCR) is deactivated by enhancing the GTPase activity of G-protein using the RGS, and the inhibition of the RGS4 activity may enhance the OR-mediated antinociceptive effect. De novo mutations in dynamin, which is one of GTPases, have been reported to cause epileptic encephalopathy by inducing a vesicular-cutting dysfunction in synaptic vesicle endocytosis (Dhindsa R S et al., 2015). However, no specific relationship between endocytosis and pain-inducing mechanisms has been reported.

Based on these studies, the present inventive concept provides a composition that can be applied for the treatment of neuropathic pain without causing a side effect, the composition including: an α2AR agonist; and an RGS inhibitor, an endocytosis inhibitor, or a combination thereof.

SUMMARY

One or more embodiments include a pharmaceutical composition for relieving pain, including: an alpha 2 (α2)-adrenoceptor agonist; a regulator of G-protein signaling (RGS) inhibitor, an endocytosis inhibitor, or a combination thereof; and a pharmaceutically acceptable salt.

One or more embodiments include a method of relieving pain of a subject, comprising: administering the pharmaceutical composition to a subject.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
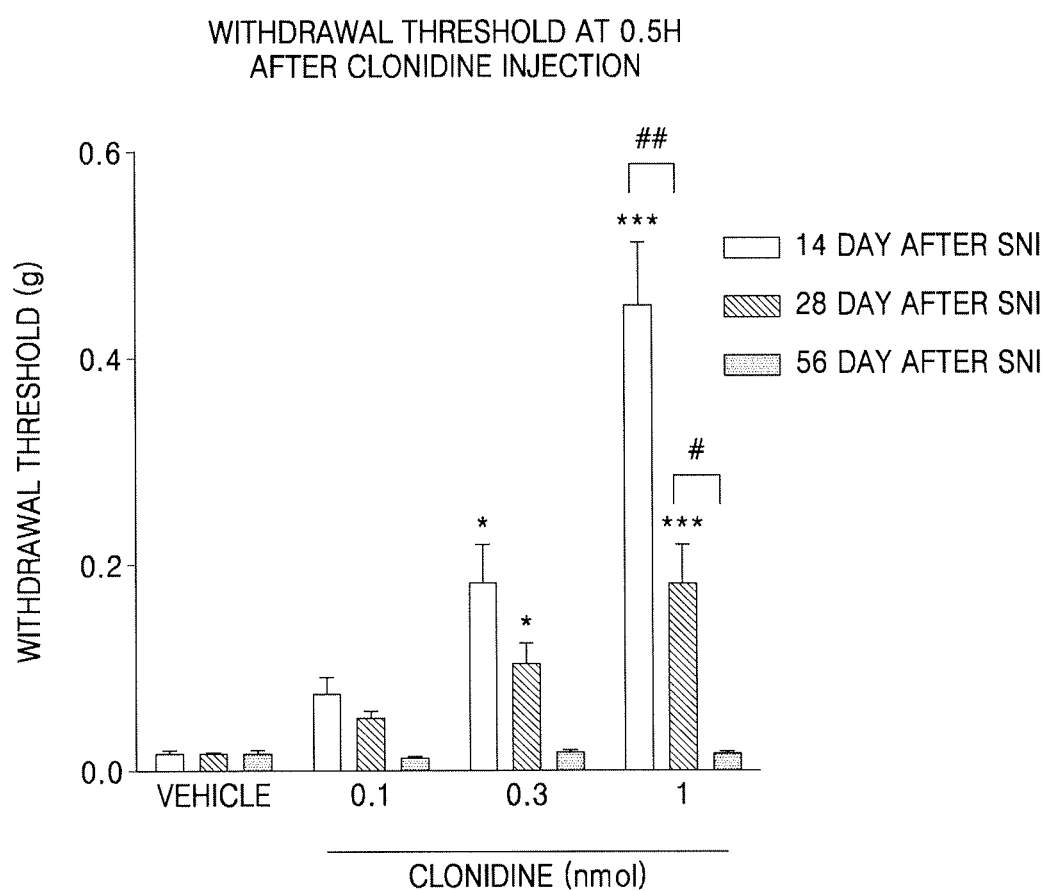
FIG. 1 shows values of withdrawal threshold for the analgesic efficacy of clonidine at each pain progression stage based on von Frey test using mice having neuropathic pain induced by a spared nerve injury (SNI)

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

An aspect of the present inventive concept provides a pharmaceutical composition for relieving pain, the composition including: an alpha 2 (α2)-adrenoceptor agonist; an inhibitor of a regulator of G-protein signaling (RGS), an endocytosis inhibitor, or a combination thereof; and a pharmaceutically acceptable salt.

In one or more embodiments, the composition may include an α2-adrenoceptor agonist and a RGS4 inhibitor;

an α2-adrenoceptor agonist and an endocytosis inhibitor; or an α2-adrenoceptor agonist, a RGS4 inhibitor, and an endocytosis inhibitor, as active ingredients.

The term 'α2-adrenoceptor agonist' used herein refers to a substance that specifically binds to an α2 subclass of an adrenergic receptor and causes receptor activity, and is used with the same meaning as 'an α2-receptor agonist', or 'an α2-adrenoceptor activator'.

Among three subtypes of $α2_A$, $α2_B$, and $α2_C$ in the α2-adrenoceptor, an $α2_A$-adrenoceptor ($α2_A$AR) has known to be involved in regulation of blood pressure, pain perception, volatile anesthetic sparing, analgesia, and working memory enhancement (Lu, et al., 2010). In this regard, the α2-adrenoceptor may refer to the $α2_A$AR. The term 'α2-adrenoceptor' is used with the same meaning as 'an α2-adrenoreceptor', or 'an α2-adrenergic receptor'.

However, the α2-adrenoceptor agonist may also have affinity towards other α2 subtypes or α1-adrenoceptor.

In one or more embodiments, examples of the α2-adrenoceptor agonist include 4-NEMD, 7-Me-marsanidine, agmatine, apraclonidine, Brimonidine, cannabigerol, clonidine, detomidine, dexmedetomidine, fadolmidine, guanabenz, guanfacine, lofexidine, marsanidine, medetomidine, methamphetamine, mivazerol, rilmenidine, romifidine, talipexole, tiamenidine, tizanidine, tolonidine, xylazine, xylometazoline, or a combination thereof, but embodiments are not limited thereto. In one or more embodiments, the α2-adrenoceptor agonist may be clonidine or dexmedetomidine.

The inventors of the present inventive concept discovered that the pain relief efficacy of the α2-adrenoceptor agonist observed at the earlier stage of neuralgia was lost at the later stage, i.e., at the chronic neuralgia. However, when co-administered with an RGS4 inhibitor, the pain relief efficacy of the α2-adrenoceptor agonist that has been lost or reduced at the later stage of neuralgia was restored. Therefore, the pharmaceutical composition for relieving pain according to the present inventive concept may include an α2-adrenoceptor agonist, an RGS4 inhibitor, and a pharmaceutically acceptable salt.

The term 'regulator of G-protein signaling (RGS)' as used herein is regarded as a protein structural domain that activates GTPase, and is used with the same meaning as a 'G-protein signal regulatory domain', 'a G-protein signal regulatory protein', or 'a G-protein signal regulatory polypeptide'. GTP is hydrolyzed by an α subunit of a G protein that is heterotrimer, so that a G-protein-coupled receptor signaling system is rapidly blocked. Examples of a protein having the domain of the regulator of G-protein signaling are ADRBK1, ADRBK2, AXIN1, AXIN2, GRK1, GRK4, GRK5, GRK6, GRK7, RGS1, RGS2, RGS3, RGS4, RGS5, RGS6, RGS7, RGS8, RGS9, RGS10, RGS11, RGS12, RGS13, RGS14, RGS16, RGS17, RGS18, RGS19, RGS20, RGS21, RK, or SNX13, but are not limited thereto. The inhibitor of the regulator of G-protein signaling may vary depending on types of the regulator of G-protein signaling. When the regulator of G-protein signaling is RGS4, the inhibitor of the regulator of G-protein signaling may be 4-[(4-fluorophenyl)methyl]-2-(4-methylphenyl)-1,2,4-thiadiazolidine-3,5-dione (CCG50014). The CCG50014 which is an inhibitor of RGS4 and RGS8 inhibits the binding of RGS protein to Gαi/0 by irreversibly binding to the RGS protein, so that the GTPase activity of Gα may be inhibited. Accordingly, in one or more embodiments, the regulator of G-protein signaling may be RGS4 or RGS8. In one or more embodiments, the inhibitor of RGS4 may be CCG50014, CCG 2046, CCG-63802, CCG-4986, CCG-203769, or a combination thereof.

In addition, the inventors of the present inventive concept assumed that the efficacy of the α2-adrenoceptor agonist would be reduced by α2-adrenoceptor endocytosis through the RGS4-mediated mechanism, and confirmed that the endocytosis inhibitor actually restored the efficacy of the α2-adrenoceptor agonist so that the reduced pain-relieving effect of the α2-adrenoceptor agonist was increased again by co-administration with the endocytosis inhibitor. Therefore, the pharmaceutical composition for relieving pain may include an α2-adrenoceptor agonist, an endocytosis inhibitor, and a pharmaceutically acceptable salt.

The term 'endocytosis' as used herein may be used in the same meaning as 'phagocytosis', 'intracellular uptake', and 'absorption of cellular debris', and may also refer to transport of an extracellular substance, such as a protein, a monosaccharide, a polysaccharide, a fatty acid, and a compound, into a cell by conjugating the extracellular substance thereto. In a molecular biological concept, endocytosys may be classified into clathrin-dependent or clathrin-independent endocytosis, or dynamin-dependent or dynamin-independent endocytosis, but embodiments are not limited thereto. The term 'inhibitor' as used herein may be used in the same meaning as 'a suppressor' or 'a blocker'.

In one or more embodiments, examples of the endocytosis inhibitor include dynasore, dynole, methyl-beta-cyclodextrin, Bis-T, MitMAB, OctMAB, pitstop-1, pitstop-2, chlorpromazine, chloroquine, or a combination thereof, but embodiments are not limited thereto. In one or more embodiments, dynole may be an indole-based dynamin inhibitor, such as dynole 34-2.

The pharmaceutical composition for relieving pain according to the present inventive concept may be configured to relief inflammatory pain, visceral pain, somatic pain, superficial somatic pain, deep somatic pain, cancer pain, somatic referred pain, or neuropathic pain. The term 'inflammatory pain' as used herein refers to pain caused by changes in the environment of cells due to activation of an immune system by hyperactivity thereof, or addition of intracellular contents or substances activated by tissue damage into extracellular fluid. The terms 'somatic pain' and 'visceral pain' as used herein refer to nociceptive pain, and more particularly, to pain caused by a stimulus that is applied to a nociceptor and travels a typical pain pathway along the pain spinal cord, the thalamus, and the cerebrum. The term 'superficial somatic pain' as used herein refers to pain caused by a mechanical, chemical, or thermal stimulus on the skin or mucous membranes, and such superficial somatic pain may be confined to a local area. The term 'deep somatic pain' as used herein refers to pain caused by stimulation of joints, ligaments, muscles, or fascia, and may occur not only locally but also broadly. The term 'somatic referred pain' as used herein is used with the same meaning as 'synalgia', and refers to pain at a body site rather than a site from which the pain is caused when the pain is severe. The term 'visceral pain' as used herein refers to dull pain felt deeply in the body by nociceptive fibers distributed in the viscera. The visceral pain may include distinct pain, such as abdominal pain. However, in consideration of small distribution of nociceptive fibers in the viscera, the visceral pain may also involve pain accompanied by various autonomic symptoms, such as nausea and vomiting, without distinct pain. In addition, the visceral pain may also involve parietal pain at the central part of the diaphragm, which belongs to the internal structure and is dominated by the nociceptive fibers of the somatic nerve, and at the pericardium, parietal pleura and parietal peritoneum. The term 'neuropathic pain' as used herein refers to pain caused by nerve damage or abnormal nerve function, and may also include spontaneous pain, which occurs even when there is no nociception stimulation, allodynia, which is caused by stimuli that normally do not cause pain, hyperalgesia, which is worsened by noxious stimulus, and other abnormal responses, such as paresthesia or dysesthesia. When the 'neuropathic pain' is divided into a central type and a peripheral type, the central neuropathic pain may be caused by damage to the central nervous system, which stimulates the spinal cord, brain stem, thalamus, and cortex, such as brain tumor, cerebral hemorrhage, syringomyelia, and acquired immune deficiency syndrome. The peripheral neuropathic pain may refer to pain caused by abnormalities of the peripheral nervous system, such as postherpetic neuralgia, diabetic neuropathy, and complex regional pain syndrome type II (Duck Mi Yoon, 2011). The term 'cancer pain' as used herein refers to cancer-induced pain. According to a three-step analgesic ladder created as a guideline for cancer pain management and advocated by the World Health Organization (WHO), it is advised as follows: Step 1: Non-opioid analgesic for mild pain, Step 2: Opioid analgesic for moderate pain, and Step 3: strong opioid analgesic for strong pain. The pain degree is varied, and for example, when the pain is severe, it is regarded as an emergency to be promptly treated, and may be associated with pain that is so severe as to cause general weakness, mental illness, and the like. Thus, such pain may refer to pain requiring active pain relief treatment classified differently from other pain causes.

Chronic pain means that acute pain caused by inflammation, contusion, and other diseases continues long time despite the cause of the acute pain disappears. In particular, neuralgia is a seizure-like pain along a certain nerve pathway, and depending on the distribution and dominance of the peripheral nervous system, neuralgia occurs convulsively and persistently from the pain of numbness to the acute pain. Chronic neuralgic among the neuralgia may include, for example, diabetic neuritis by diabetic complication, postherpetic pain, numbness by limb nerve injury, paralysis, numbness or pain in the lower limb by spinal cord compression, pain following nerve injury by fracture, and pain following spinal surgery.

As confirmed by the inventors of the present inventive concept, the α2-adrenoceptor agonist has the pain relief effect at the earlier stage of the neuropathic pain induced with SNI in mouse when administered at a low dose. However, at the later stage, i.e., in the case of the mouse model of chronic neuropathic pain, the α2-adrenoceptor agonist no longer exhibits the pain relief effect. To obtain the pain relief effect, a high dose of the α2-adrenoceptor agonist is then required. However, when the α2-adrenoceptor agonist was co-administered with a RGS4 inhibitor or an endocytosis inhibitor, the pain relief effect of the α2-adrenoceptor agonist in the mouse model of chronic neuropathic pain was restored even at the chronic stage. Therefore, the pharmaceutical composition for relieving pain according to an embodiment may be used to relieve pain at the chronic neuropathic pain stage.

In one or more embodiments, the pharmaceutical composition for relieving pain may be intended to improve side effects of the α2-adrenoceptor agonist. When administered at a high dose to a mammal, symptoms such as sedation, muscle relaxation, sleeping action, thirst, hypogonadism, helplessness, constipation, dizziness, and especially low blood pressure, along with the analgesic action. Thus, when the α2-adrenoceptor agonist is used for the neuropathic pain, it is practically difficult to use the α2-adrenoceptor agonist due to the above-mentioned side effects. Particularly, in the case of the chronic neuropathic pain, at least 10-fold higher dose of drug than a drug for the neuropathic pain at the early stage is required in the animal experiments carried out by the inventors of the present inventive concept. In this case, however, severe low blood pressure and mobility reduction symptoms occur (see FIGS. 7 and 8). Thus, when using the α2-adrenoceptor agonist with an inhibitor of RGS or with an endocytosis inhibitor, the α2-adrenoceptor agonist may be administered at a low dose, so that the pharmaceutical composition according to the present inventive concept may enable the α2-adrenoceptor agonist to be used for relieving pain, especially, chronic neuropathic pain.

When a mammal including a human is to a target of the administration, a dose of clonidine in the composition according to an embodiment may be, per kilogram of subject weight, in a range of about 0.1 µg to about 450 µg, about 0.1 µg to about 400 µg, about 0.1 µg to about 350 µg, about 0.1 µg to about 300 µg, about 0.1 µg to about 250 µg, about 0.1 µg to about 200 µg, about 0.1 µg to about 150 µg, about 0.1 µg to about 100 µg, about 0.1 µg to about 80 µg, about 0.1 µg to about 50 µg, about 0.1 µg to about 30 µg, about 0.1 µg to about 25 µg, about 0.1 µg to about 20 µg, about 0.1 µg to about 15 µg, about 0.1 µg to about 10 µg, about 1 µg to about 50 µg, about 15 µg to about 50 µg, about 20 µg to about 50 µg, about 1 µg to about 30 µg, about 10 µg to about 30 µg, about 15 µg to about 30 µg, about 20 µg to about 30 µg, 0.5 µg to about 25 µg, about 1 µg to about 25 µg, about 5 µg to about 25 µg, about 10 µg to about 25 µg, about 1 µg to about 20 µg, about 5 µg to about 20 µg, about 10 µg to about 20 µg, about 15 µg to about 20 µg, about 1 µg to about 10 µg, about 5 µg to about 10 µg, about 8 µg to about 10 µg, about 0.1 µg to about 5 µg, about 0.5 µg to about 5 µg, about 1 µg to about 5 µg, about 0.1 µg to about 1 µg, or about 0.5 µg to about 1 µg. However, a volume including such a dose above and usage of the drug may vary depending on the age, body weight, gender, dosage form, health condition, and disease severity of a patient. When clonidine is used in a healthy adult male for analgesic or anesthetic purposes, no side effect is shown when administered in a concentration gradient from about 150 µg to about 450 µg. When 1 µg/kg of clonidine is administered intravenously with lidocaine, no statistically significant side effects is shown. When 5 µg/kg of clonidine is administered orally, it is reported that no harmful side effect is shown (Richard G, et al., 2010). When a commercially available drug (Kabvay SR Tablet), for example, a clonidine salt, is used as a therapeutic drug for ADHD, clinical studies on child and adolescents (6 to 17 years old) revealed that, in the case of the administration of about 0.2 mg/day to about 0.4 mg/day at once to 78 patients in a test group, about 31% and about 19% of the patients complain drowsiness and headache side effects, respectively, and symptoms of low blood pressure are not reported. In the clinical test, the average change in systolic blood pressure from which the maximal placebo effect is removed is, in the case of the administration of 0.2 mg/day, about −4.0 mmHg, and the average change in diastolic blood pressure is about, in the case of the administration of 0.2 mg/day, about −4.0 mmHgl. Accordingly, a dose of clonidine (0.2 mg) is not considered to substantially induce low blood pressure. That is, based on the concentrations known to cause side effects of the α2-adrenoceptor agonist, a one-time maximum dose of clonidine is about 450 µg, and more preferably, about 0.2 mg. Therefore, in one or more embodiments, when the pharmaceutical composition for relieving pain is administered to a subject, about 0.45 mg or less of, preferably, about 0.2 mg or less of clonidine may be used for the administration. In addition, when the α2-adrenoceptor agonist in the pharmaceutical composition for relieving pain is clonidine, about 0.45 mg or less of, preferably, about 0.2 mg or less of clonidine may be used for the administration.

When a mammal including a human is to a target of the administration, a dose of dexmedetomidine in the composition according to an embodiment may be, per kilogram of subject weight, in a range of about 0.1 µg to about 450 µg, about 0.1 µg to about 400 µg, about 0.1 µg to about 350 µg, about 0.1 µg to about 300 µg, about 0.1 µg to about 250 µg, about 0.1 µg to about 200 µg, about 0.1 µg to about 150 µg, about 0.1 µg to about 100 µg, about 0.1 µg about 80 µg, about 0.1 µg to about 50 µg, about 0.1 µg to about 25 µg, about 0.1 µg to about 10 µg, about 1 µg to about 50 µg, about 10 µg to about 50 µg, about 25 µg to about 50 µg, about 1 µg to about 25 µg, about 10 µg to about 25 µg, about 15 µg to about 25 µg to about 10 µg, about 0.5 µg to about 10 µg, about 0.8 µg to about 10 µg, about 1 µg to about 10 µg, about 2 µg to about 10 µg, about 5 µg to about 10 µg, about 8 µg to about 10 µg, about 0.5 µg to about 5 µg, about 0.1 µg to about 1 µg, or about 0.5 µg to about 1 µg. However, a volume including such a dose above and usage of the drug may vary depending on the age, body weight, gender, dosage form, health condition, and disease severity of a patient. Based on the concentrations known to cause side effects of the α2-adrenoceptor agonist, when dexmedetomidine is administered to a human subject for analgesic or anesthetic purposes and 0.5 µg/kg of dexmedetomidine is administered intravenously in combination with lidocaine, no statistically significant side effects is shown. When about 5 µg/kg to about 10 µg/kg of dexmedetomidine is administered intravenously, it is reported that no incidental respiratory paralysis is shown (Richard G, et al., 2010). In addition, dexmedetomidine may be clinically used as hydrochloride, and then, may be injected at a loading dose of about care. Here, to maintain sedation under intensive care, dexmedetomidine may be injected up to about 0.2 µg/kg/hour to about 0.7 µg/kg/hour, and patients with low blood pressure of about 25% are reported within 24 hours. Therefore, regarding the α2-adrenoceptor agonist in the pharmaceutical composition for relieving pain, when the α2-adrenoceptor agonist is dexmedetomidine, it is found that about 10 µg/kg or less, preferably, about 0.2 µg/kg of dexmedetomidine is administered.

The term 'pharmaceutically acceptable salt' as used herein may be used with the same meaning as 'pharmaceutically acceptable carrier', and refers to an organic or inorganic addition salt of a compound represented by Formula S in a concentration that is relatively non-toxic and harmless to a patient and has a harmless effective action so that side effects caused by the salt do not impair beneficial efficacy of the compound of Formula S. The salt of the compound may be both inorganic and organic acids. Examples of the inorganic acid are hydrochloric acid, bromic acid, nitric acid, sulfuric acid, perchloric acid, and phosphoric acid, and examples of the organic acid are citric acid, acetic acid, lactic acid, maleic acid, fumaric acid, gluconic acid, methanesulfonic acid, gluconic acid, succinic acid, tartaric acid, galacturonic acid, embonic acid, glutamic acid, aspartic acid, oxalic acid, (D) or (L) malic acid, methanesulfonic acid, ethanesulfonic acid, 4-toluenesulfonic acid, salicylic acid, benzoic acid, and malonic acid. In addition, the salt may include an alkali metal salt (e.g., a sodium salt and a potassium salt) and an alkaline earth metal salt (e.g., a calcium salt and a magnesium salt). For example, an acid addition salt may include acetate, aspartate, benzoate, be besilate, bicarbonate/carbonate, bisulfate/sulfate, borate, camsylate, citrate, edisylate, formate, fumarate, gluceptate, gluconate, glucuronate, hexafluorophosphate, hybenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccchrate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, and zinc salt. For example, the acid addition salt may be hydrochloride or trifluoroacetate.

Another aspect of the present inventive concept provides a method of relieving pain including administering the pharmaceutical composition for relieving pain to a subject. In one or more embodiments, the administering of the pharmaceutical composition for relieving pain to the subject may be performed by simultaneously, individually, or sequentially administering an α2-adrenoceptor agonist; and an inhibitor of a regulator of G-protein signaling (RGS), an endocytosis inhibitor, or a combination thereof.

Regarding the administration in consideration of oral administration or non-oral administration including intravenous, intraperitoneal, intradermal, subcutaneous, epithelial, or muscular administration, the pharmaceutical composition may include a pharmaceutically acceptable carrier suitable for each of the administration method, and then, administered in various dosage forms. When formulated, the pharmaceutical composition may be prepared using filler that is generally used, an extender, a binder, a wetting agent, a disintegrating agent, a diluent including a surfactant, or an excipient.

Solid formulations for oral administration include tablets, pills, powders, granules, capsules, or troches. Such solid formulations may be prepared by mixing at least one compound of the present inventive concept with at least one excipient, such as starch, calcium carbonate, sucrose or lactose, or gelatin. In addition, when formulated, in addition to a simple excipient, a lubricant, such as magnesium stearate talc, may be used. Liquid formulations for oral administration include suspensions, solutions, emulsions, or syrups. Such liquid formulations may include, in addition to water, which is simple diluents, and liquid paraffin, a variety of excipients, such as wetting agents, sweetening agents, fragrances, and preservatives.

Formulations for non-oral administration may include sterilized solutions, non-aqueous solutions, suspensions, emulsions, freeze-dried preparations, and suppositories. As non-aqueous solutions and suspensions, propylene glycol, polyethylene glycol, vegetable oil such as olive oil, and injectable ester such as ethyl oleate may be used. Examples of suppositories include witepsol, macrogol, tween 61, cacao butter, laurin, glycerol, and gelatine.

In one or more embodiments, the α2-adrenoceptor agonist in the pharmaceutical composition for relieving pain that is to be administered according to the method may be contained in a dose not causing the low blood pressure or a dose reducing the incidence of low blood pressure. Such a dose not causing side effects including the low blood pressure may vary depending on the age, body weight, gender, dosage form, health condition, and disease severity of a patient. However, according to the results related to the low blood pressure and the mobility reduction among the side effects shown in the animal models of the experiments carried by the inventors of the present application, the pharmaceutical composition for relieving pain of the present inventive concept may be required only in a volume of about 10% of a single dose of the α2-adrenoceptor agonist that is administered to achieve the same effect. Therefore, it is easy to predict that the side effects of the α2-adrenoceptor agonist are either absent or may be improved. Clonidine is a drug that is currently used as a therapeutic agent for hypertension, but in consideration of elderly patients who suffer from chronic neuropathic pain and hypertension at the same time, the pharmaceutical composition for relieving pain may be beneficial for relieving chronic neuropathic pain and hypertension at the same time as being administered in a dose within a range not causing a side effect including low blood pressure.

In one or more embodiments, the subject in the method of alleviating the pain may be a mammal. The mammal may be a human, and the effective dose of the compound of the present inventive concept with respect to the human body may vary depending on the age, body weight, gender, dosage form, health condition, and disease severity of a patient.

Hereinafter, one or more embodiments will be described in more detail with reference to the following examples. However, these examples are not intended to limit the scope of the present disclosure.

Example 1: Analgesic Efficacy of α2-Adrenoceptor in Neuralgic Mice

To confirm analgesic efficacy of an α2-adrenoceptor, neuralgic mouse models were used to evaluate a pain relief effect of each α2-adrenoceptor according to neuralgia stages.

(1) Preparation of a Neuralgic Mouse Model

To prepare neuralgia-induced mouse models, mice having a genetic background of 129S4/SvJae×C57BL/6J were used. According to a modification of the method described in the related art, a spared nerve injury (SNI) of sciatic nerve was induced in the mice [1][2].

Briefly, the mice were anesthetized with 3% isoflurane in a mixture of $N_2O/O_2$ gas. At the right hindlimb, incision was made at a mid-thigh level, and peripheral branches (sural, common peroneal, and tibial nerves) of the sciatic nerve were exposed. Both tibial and common peroneal nerves were tightly ligated with 8.0 silk thread together, and a 1-2 mm section of the two nerves was removed. The sural nerve was carefully preserved by avoiding any nerve stretch or nerve contact with surgical tools. Muscle and skin were closed in two distinct layers with chromic catgut 6.0 and silk 6.0 suture, respectively. During recovery, animals were housed in clear plastic cages with a thick layer of sawdust bedding.

(2) Intrathecal Drug Administration

CCG50014 (4-[(4-fluorophenyl)methy]-2-(4-methylphenyl)-1,2,4-thiadiazolidine-3,5-dione, RGS4 inhibitor) and Dexmedetomidine (4-[(1S)-1-(2,3-dimethylphenyl)ethyl]-1H-imidazole hydrochloride, alpha2AR agonist) were purchased from Tocris (Bristol, UK). Clonidine (2-[(2,6-dichlorophenyl)amino-2-imidazoleine hydrochloride, alpha2AR agonist) was purchased from Sigma (St. Louis, Mo., USA). CCG50014 was diluted in 12% dimethyl sulfoxide (DMSO) in saline. Dexmedetomidine and clonidine were diluted in saline.

Each drug was administered by intrathecal injection based on the technique developed by Hylden and Wilcox. 20 drugs were dissolved in 5 μl of vehicle. Briefly, for mouse intrathecal injections, a 30-gauge needle (length: 0.5 inch) connected to a 50 μl Hamilton syringe was inserted into the subarachnoid space between the lumbar vertebrae L5 and L6. A flick of the mouse tail provided a reliable indicator that the needle had penetrated the dura meter. The syringe was held in position for a few seconds after the injection of 5 μl/mouse.

(3) Pain Behavioral Evaluation (Von-Frey Test)

To evaluate a degree of pain alleviation in each of the neuralgic mice, a degree of pain responses to mechanical stimuli was measured by measuring mechanical threshold based on the method described in the related art. In detail, mechanical withdrawal thresholds were determined for all mice at day 0 prior to neuropathic surgery in order to obtain normal baseline values of withdrawal threshold to mechanical stimuli. For 56 days post-SNI surgery, all experimental animals were behaviorally tested to confirm the development of mechanical allodynia. At 14, 29, or 56 days after SNI, mice were randomly assigned and the analgesic effect of single intrathecally injected clonidine or dexmedetomidine was subsequently examined. The test was performed using an ascending series of von Frey filaments (North Coast Medical, Morgan Hill, Calif.). Mice were placed in an acrylic cylinder (6.5 cm in diameter and 17 cm in height) on an elevated metal mesh grid and allowed to acclimate for 30 minutes before testing. Each monofilament (0.008 g, 0.02 g, 0.07 g, 0.16 g, 0.4 g, and 0.6 g) was applied 6 times in ascending order to the midplantar region of each hind paw of mouse. The monofilament that produced a paw withdrawal, flinch, or lick in 3 of 6 applications was defined as the 50% paw withdrawal threshold. The behavioral investigator was blinded to the treatment of animals during the experiments. CCG50014 or dynasore was intrathecally injected 5 minutes before clonidine or dexmedetomidine treatment.

Results of each of the experiments above are expressed as means±SEM unless otherwise stated. Data analysis and statistical comparisons were performed using GraphPad Prism version 5.0 (GraphPad Software, San Diego, Calif.). Comparison between two groups was made using the Student's t-test. For multiple comparisons, ANOVA followed by post hoc Tukey test was performed. Differences with $P<0.05$ were considered significant.

Figure 2:
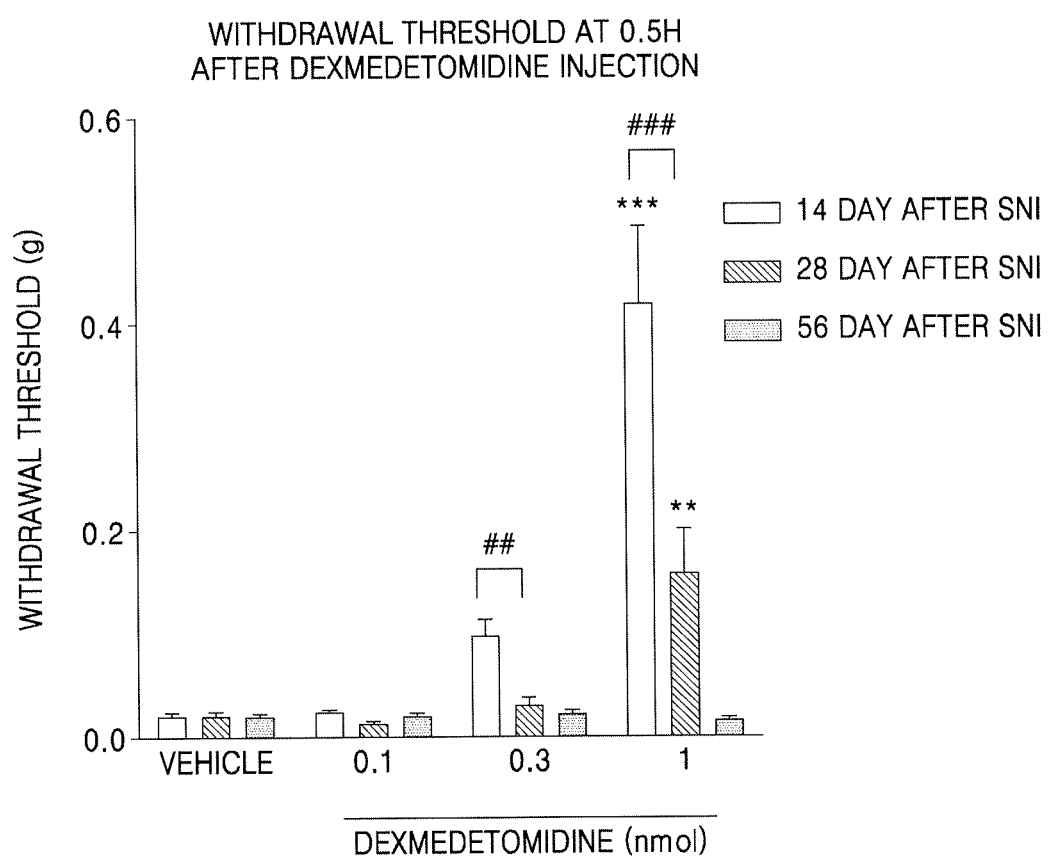
FIG. 2 shows the analgesic efficacy of dexmedetomidine in the same experiment.

As a result, as shown in FIGS. 1 and 2, the neuropathic pain induced by SNI in mouse was alleviated by clonidine and dexmedetomidine. However, at 14 days after SNI, clonidine and dexmedetomidine potent analgesic effect as doses of both clonidine and dexmedetomidine increased, whereas such analgesic effect was decreased at 28 days and finally completely disappeared at 56 days after SNI.

Figure 5:
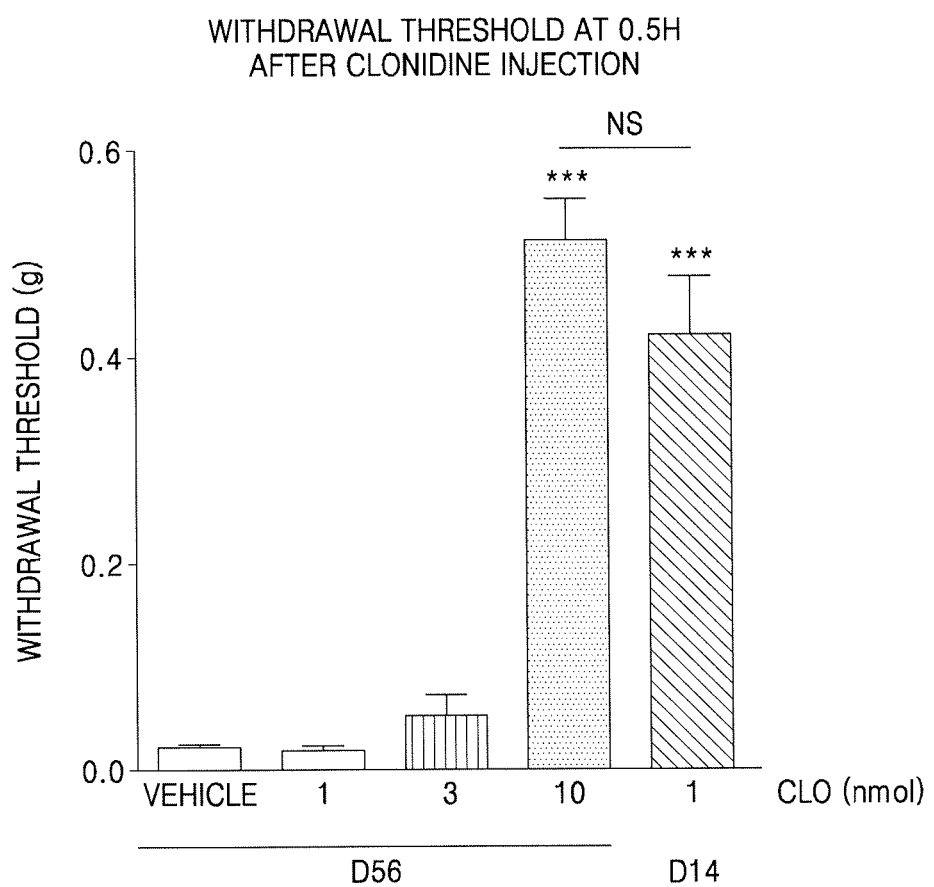
FIG. 5 shows values of withdrawal threshold for the analgesic efficacy upon a dose of clonidine at 56 and 14 days in mice having neuropathic pain induced by SNI.
Figure 6:
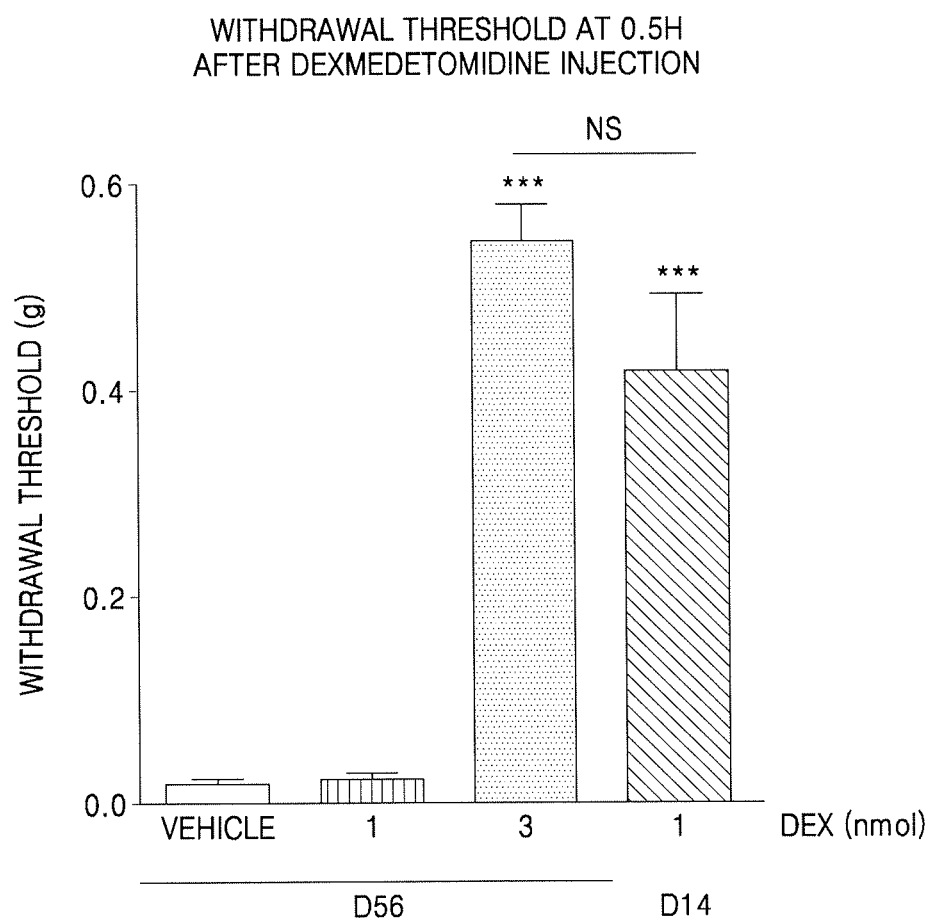
FIG. 6 shows the analgesic efficacy of dexmedetomidine in the same experiment.

The loss of the efficacy of the α2-adrenoceptor agonist in the chronic stage was clearly shown when compared with the effective analgesic dose of clonidine and dexmedetomidine at 14 or 56 days or after SNI with respect to the analgesic effects thereof. Referring to FIGS. 5 and 6, at 14 days after SNI, 1 nmol of clonidine or dexmedetomidine showed the significant analgesic effect, but at 56 days after SNI, 10-fold (clonidine) or 3-fold (dexmedetomidine) higher dose of drugs showed the analgesic effect similar to that at 14 days after SNI.

That is, the α2-adrenoceptor agonist, such as clonidine and dexmedetomidine, exhibited the analgesic efficacy at the earlier stage of the neuropathic pain. However, at the chronic stage, it was found that both clonidine and dexmedetomidine lost the analgesic efficacy.

Figure 3:
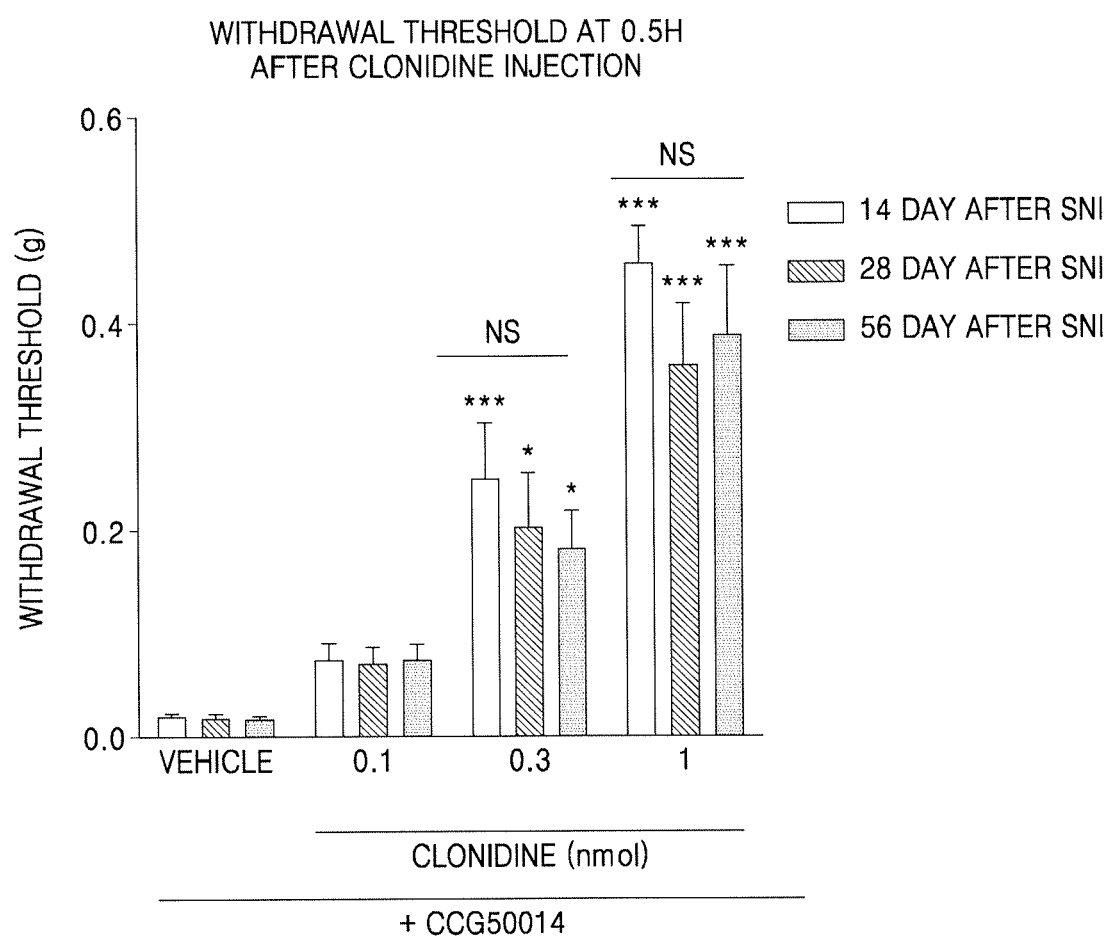
FIG. 3 shows values of withdrawal threshold for the analgesic efficacy upon co-administration of CCG 50014 (RGS4 inhibitor) and clonidine based on von Frey test using mice having neuropathic pain induced by SNI.
Figure 4:
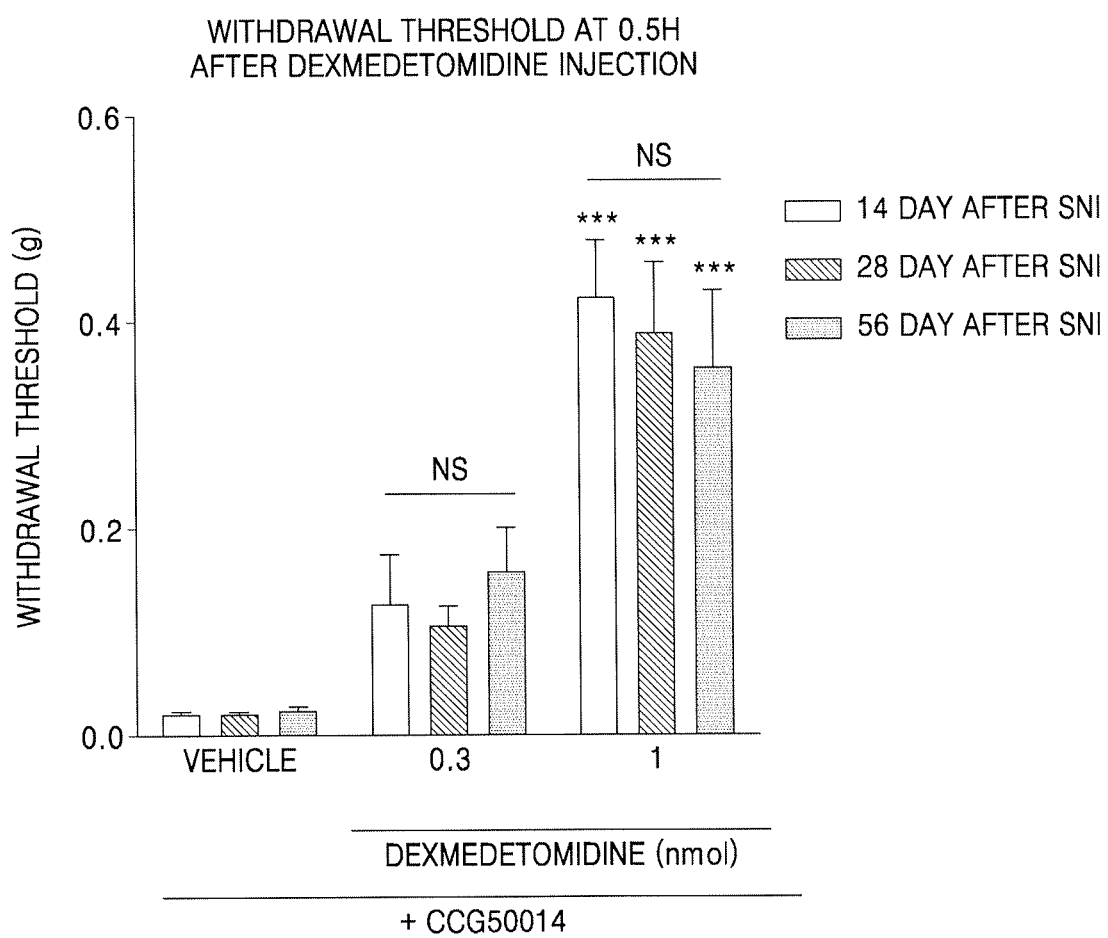
FIG. 4 shows the analgesic efficacy upon co-administration of CCG 50014 and dexmedetomidine in the same experiment.

When CCG 50014 (RGS4 inhibitor) was co-administered with clonidine or dexmedetomidine after the neuropathic pain was induced by SNI in a normal mouse, as shown in FIGS. 3 and 4, the analgesic efficacy of these drugs were maintained at 14, 28, or even 56 days after SNI. Therefore, the α2-adrenoceptor agonist may be able to restore the analgesic efficacy that was lost in the chronic stage by co-administering the α2-adrenoceptor agonist with RGS4 inhibitor into a subject. Here, a low dose of the α2-adrenoceptor agonist for the administration was expected to exhibit sufficient analgesic efficacy.

Figure 9:
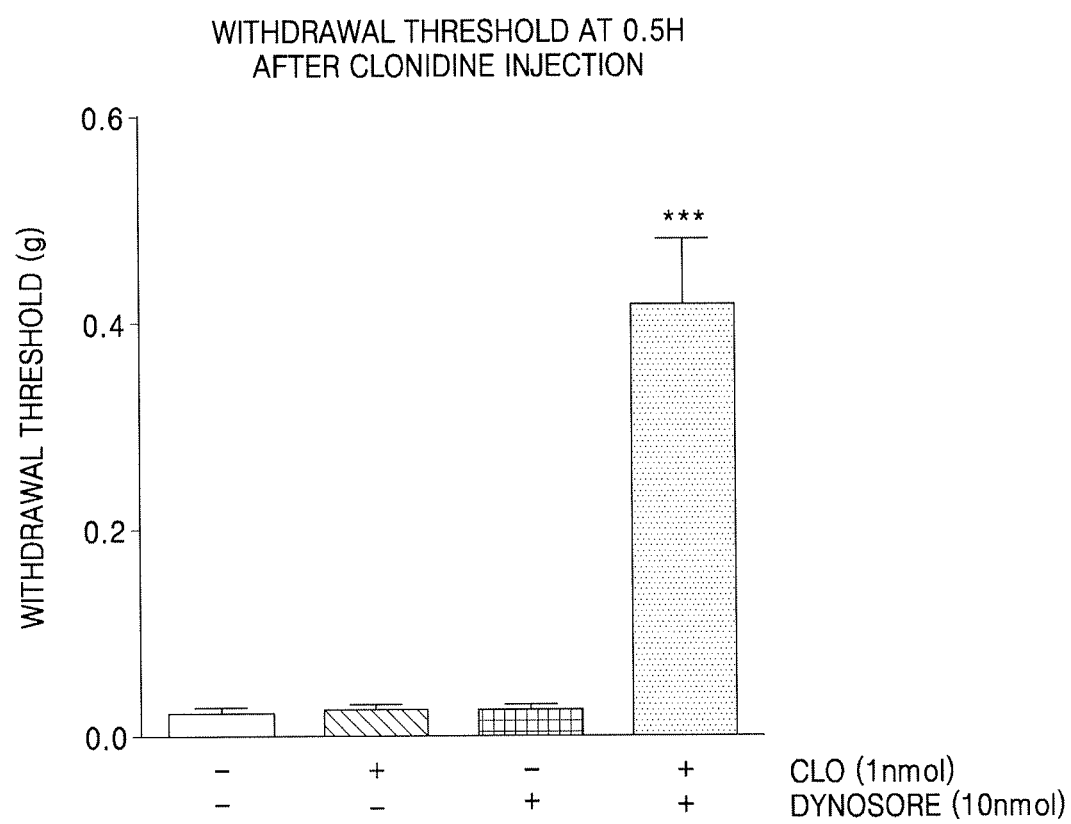
FIG. 9 shows values of withdrawal threshold for the analgesic efficacy upon co-administration of dynasore and clonidine in mice having neuropathic pain induced by SNI.

In addition, referring to FIG. 9, when dynasore was co-administered with clonidine in the mouse having the neuropathic pain induced by SNI, the analgesic efficacy of clonidine was restored by dynasore at $56^{th}$ day after SNI similar to the RGS4 inhibitor. Therefore, it was confirmed that, at the later stage of the neuropathic pain, the loss of the pain-alleviating efficacy of α2-adrenoceptor agonist was related to the endocytosis. In this regard, even in case of the administration of the α2-adrenoceptor agonist in combination with the endocytosis inhibitor, it was confirmed that the same effect as that obtained by administering with the RGS4 receptor inhibitor was expected.

Example 2: Evaluation of Overcoming Side Effects

Due to low blood pressure which is a known side effect of the α2-adrenoceptor agonist, the administration of the α2-adrenoceptor agonist at high doses may be dangerous to an individual. Thus, to evaluate whether the α2-adrenoceptor agonist caused low blood pressure at an effective dose and was able to overcome such a side effect when administered with the RGS4 inhibitor, blood pressure and motion performance capability were measured.

(1) Measurement of Blood Pressure

To evaluate the induction of low blood pressure, systolic blood pressure (SBP) was measured using a non-invasive computerized tail-cuff system as previously described in the art (PowerLab system, ADI Instrument Pry Ltd., Chain Hills, NSW, Australia). Briefly, animals were acclimated for 30 minutes in a quiet test room prior to obtaining cardiovascular measurements. At the end of the 1 hour period, the SBP was measured. This experiment was repeated 3 times and the mean value for each animal was recorded. Blood pressure was recorded at 0 and 30 minutes after treating the mice with clonidine, dexmedetomidine, the RGS inhibitor, or in combination thereof. All cardiovascular measurements were obtained between 1 pm to 3 pm in order to avoid changes due to normal circadian rhythms.

(2) Evaluation of Motion Performance Capability (Rotarod Test)

To evaluate degradation of motion performance capability as one of side effects caused by the low blood pressure, rotarod test was performed on each of the mice administered with clonidine or the RGS4 inhibitor. The rotarod test (model # DJ-4009, Dae-Jong Engineering & Clean Technology, Korea) consisted of a rotating horizontal bar (diameter of 6 cm), which was subdivided into four compartments by rotating plates. All mice were placed on the horizontal bar, which was set at a rotation speed of 4 revolutions per minutes. All mice were tested 24 hours before the actual rotarod test, and mice that were able to remain on the rod for at least 120 seconds were included in the experiment. 30 minutes after clonidine injection, each animal was subsequently tested on the rotarod over 2-minutes period and their performance time on the bar (in seconds) was measured. The test was repeated 3 times and the mean value for each animal was recorded.

Test results are expressed as means±SEM unless otherwise stated. Data analysis and statistical comparisons were performed using GraphPad Prism version 5.0 (GraphPad Software, San Diego, Calif.). Comparison between two groups was made using the Student's t-test. For multiple comparisons, ANOVA followed by post hoc Tukey test was performed. Differences with $P<0.05$ were considered significant.

Figure 7:
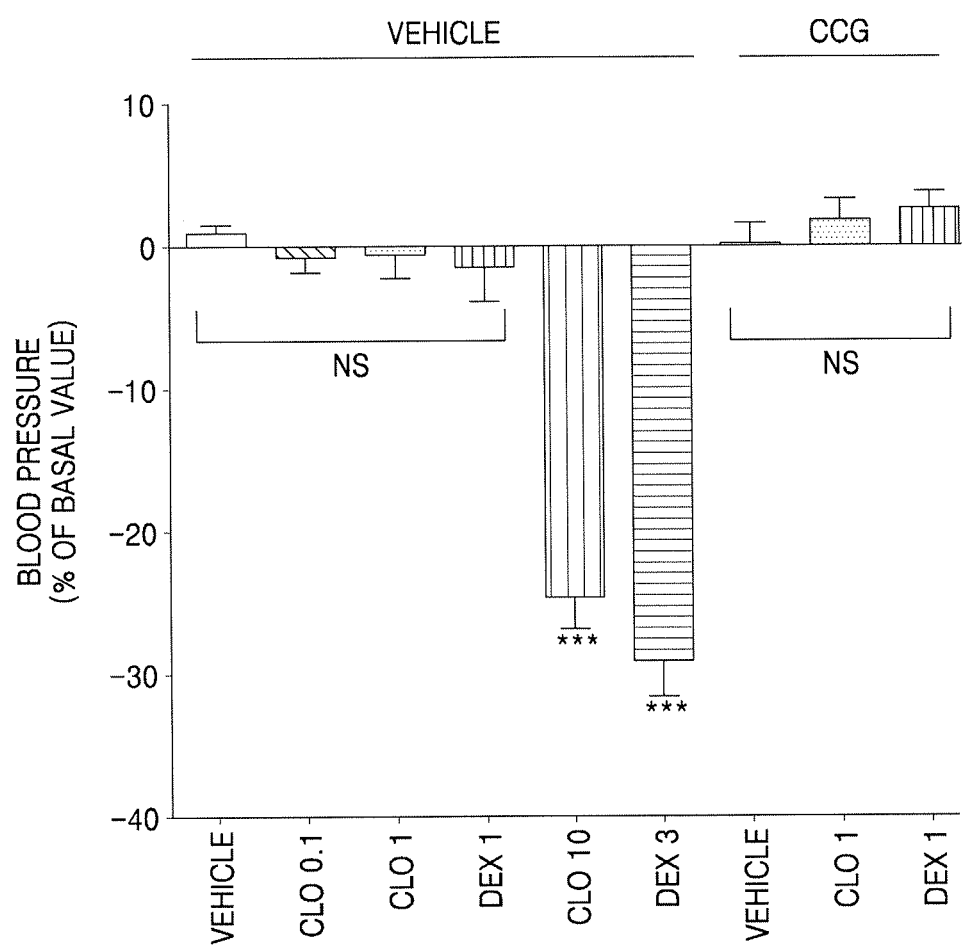
FIG. 7 shows changes in blood pressure in mice administered with clonidine or dexmedetomidine alone or in combination of CCG 50014 (RGS4 inhibitor)
Figure 8:
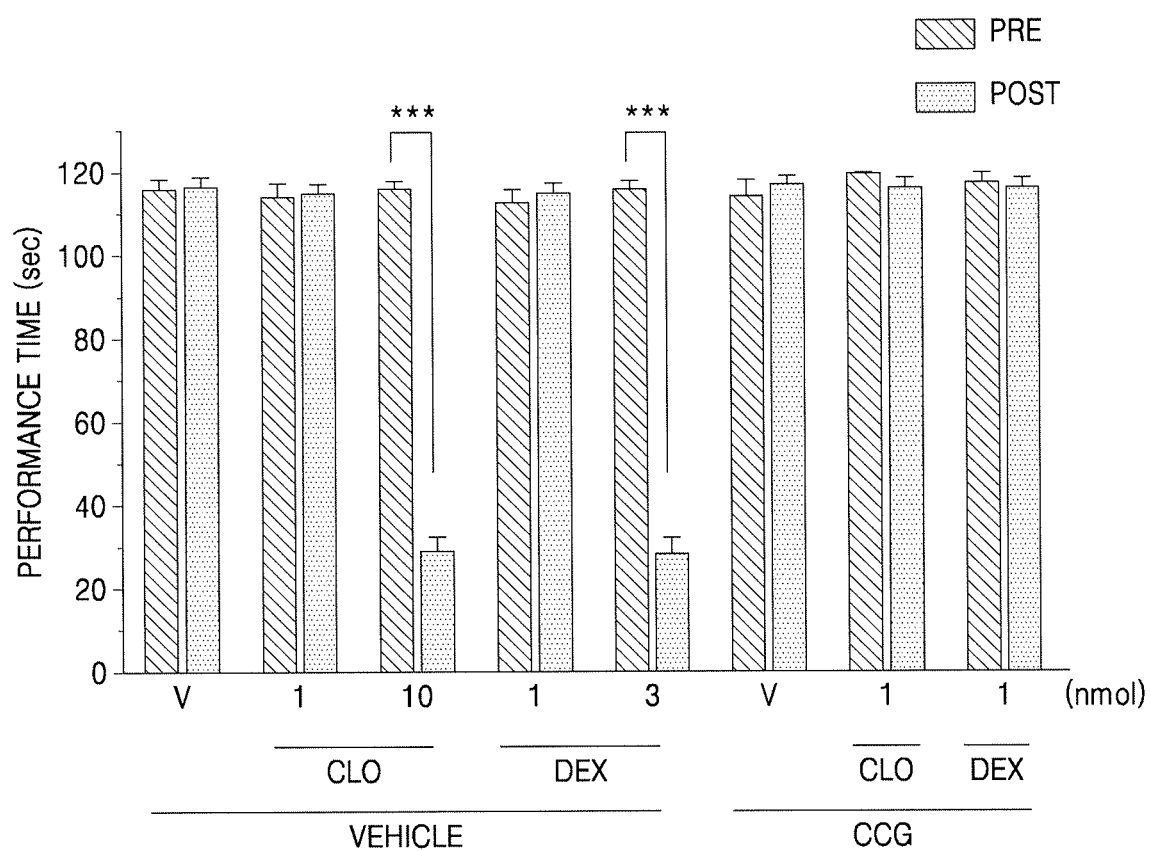
FIG. 8 shows changes in motion performance in mice administered with clonidine or dexmedetomidine alone or in combination of CCG 50014 (RGS4 inhibitor)

As a result, the effective dose of clonidine (10 nmol) and dexmedetomidine (3 nmol) showed the significant symptoms of low blood pressure as shown in FIG. 7, and rapidly decreased motor performance as shown in FIG. 8. Meanwhile, in the test mice administered in combination with the RGS4 inhibitor, the effective dose of clonidine (1 nmol) or dexmedetomidine (1 nmol) showed no side effects as described above.

Therefore, when the α2-adrenoceptor was administered in combination with the RGS4 inhibition, the α2-adrenoceptor was able to exhibit pain relief effect even at the chronic stage of the neuropathic pain when administered at a dose that caused no side effects, such as low blood pressure or degradation of motion performance.

According to one or more embodiments as described above, a pharmaceutical composition for alleviating pain, including: an α2-adrenoceptor agonist; an inhibitor of a regulator of G-protein signaling (RGS), an endocytosis inhibitor or a combination thereof; and a pharmaceutically acceptable salt, and a method of alleviating pain of a subject, including administering the pharmaceutical composition into the subject may provide a new therapeutic strategy for chronic neuropathic pain management by reducing side effects of the α2-adrenoceptor agonist and restoring and amplifying the analgesic efficacy of the α2-adrenoceptor.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

REFERENCES

1. Lu R, Chen Y, Cottingham C, Peng N, Jiao K, Limbird L E, Wyss J M, Wang Q, Enhanced Hypotensive, Bradycardic, and Hypnotic Responses to α2-Adrenergic Agonists in Spinophilin-Null Mice Are Accompanied by Increased G Protein Coupling to the α2A-Adrenergic Receptor, Mol Pharmcol. 2010; 78:279-286
2. Yoon S Y, Woo J, Park J O, Choi E J, Shin H S, Roh D H, Kim K S (2015) Intrathecal RGS4 Inhibitor, CCG50014, Reduces Nociceptive Responses and Enhances Opioid-Mediated Analgesic Effects in the Mouse Formalin Test. Anesth Analg 2015; 120: 671-7
3. Yoon S Y, Yeo J H, Han S D, Bong D J, Oh B, Roh D H, Diluted bee venom injection reduces ipsilateral mechanical allodynia in oxaliplatin-induced neuropathic mice. Biol Pharm Bull. 2013; 36 (11): 1787-93
4. Decosterd I, Woolf C J, Spared nerve injury: an animal model of persistent peripheral neuropathic pain. Pain. 2000 August; 87 (2):149-58.
5. Bourquin AF1, S?veges M, Pertin M, Gilliard N, Sardy S, Davison A C, Spahn D R, Decosterd I, Assessment and analysis of mechanical allodynia-like behavior induced by spared nerve injury (SNI) in the mouse. Pain. 2006 May; 122 (1-2): 14.e1-14.

6. Emanueli C, Fink E, Milia A F, Salis M B, Conti M, Demontis M P, Madeddu P, Enhanced blood pressure sensitivity to deoxycorticosterone in mice with disruption of bradykinin B2 receptor gene. Hypertension 1998; 31: 1278-1283.
7. Dhindsa R S, Bradrick S S, Yao X, Heinzen E L, Petrovski S, Krueger B J, Johnson M R, Frankel W N, Petrou S, Boumil R M, Goldstein D B, Epileptic encephalopathy-causing mutations in DNM1 impair synaptic vesicle endocytosis. Neurol Genet. 2015 Apr. 17; 1(1):e4.
8. Duck Mi Yoon, Analgesic therapy according to disease specific Pathophysiology, J Korean Med Assoc 2011 July; 54(7): 739-746.
9. Richard G. Ouellette, Joseph A. Joyce, Pharmacology For Nurse Anesthesiology, 2010, p 89-91.

What is claimed is:

1. A method of relieving chronic neuropathic pain of a subject, the method comprising:
administering 0.1 to 200 µg/kg of an alpha 2 ($\alpha$2)-adrenoceptor agonist to the subject in need thereof; and
administering an effective amount of an inhibitor selected from an inhibitor of a regulator of a G-protein signaling (RGS), an endocytosis inhibitor, or a combination thereof to the subject in need thereof,
wherein an effective amount of the inhibitor causes the administered alpha 2 ($\alpha$2)-adrenoceptor agonist to relieve the chronic neuropathic pain,
wherein the subject is a mammal, and
wherein the endocytosis inhibitor is dynasore or chloroquine.

2. The method of claim 1, wherein the inhibitor is the combination of the inhibitor of the RGS and the endocytosis inhibitor.

3. The method of claim 1, wherein 0.1 to 20 µg/kg of the alpha 2 ($\alpha$2)-adrenoceptor agonist is administered.

4. The method of claim 1, wherein the alpha 2 ($\alpha$2)-adrenoceptor agonist and the inhibitor are administered sequentially.

5. The method of claim 1, wherein the $\alpha$2-adrenoceptor agonist is 4-NEMD, 7-Me-marsanidine, agmatine, apraclonidine, brimonidine, cannabigerol, clonidine, detomidine, dexmedetomidine, fadolmidine, guanabenz, guanfacine, lofexidine, marsanidine, medetomidine, methamphetamine, mivazerol, rilmenidine, romifidine, talipexole, tiamenidine, tizanidine, tolonidine, xylazine, xylometazoline, or a combination thereof.

6. The method of claim 1, wherein the inhibitor comprises the inhibitor of the RGS and the RGS is RGS4 or RGS8.

7. The method of claim 1, wherein the inhibitor comprises the inhibitor of the RGS and the inhibitor of the RGS is CCG-50014, CCG-2046, CCG-63802, CCG-4986, CCG-203769, or a combination thereof.

8. The method of claim 1, wherein the method is for improving a side effect of the $\alpha$2-adrenoceptor agonist.

9. The method of claim 1, wherein the $\alpha$2-adrenoceptor agonist is administered in a dose that does not cause low blood pressure in the subject.

10. The method of claim 1, wherein the subject is a human.

11. The method of claim 1, wherein the inhibitor is the inhibitor of the RGS.

12. The method of claim 1, wherein the $\alpha$2-adrenoceptor agonist is clonidine.

13. The method of claim 1, wherein the $\alpha$2-adrenoceptor agonist is dexmedetomidine.

* * * * *